July 7, 1970 E. S. BOERNER Plant Pat. 2,979
ROSE PLANT
Filed Sept. 6, 1968
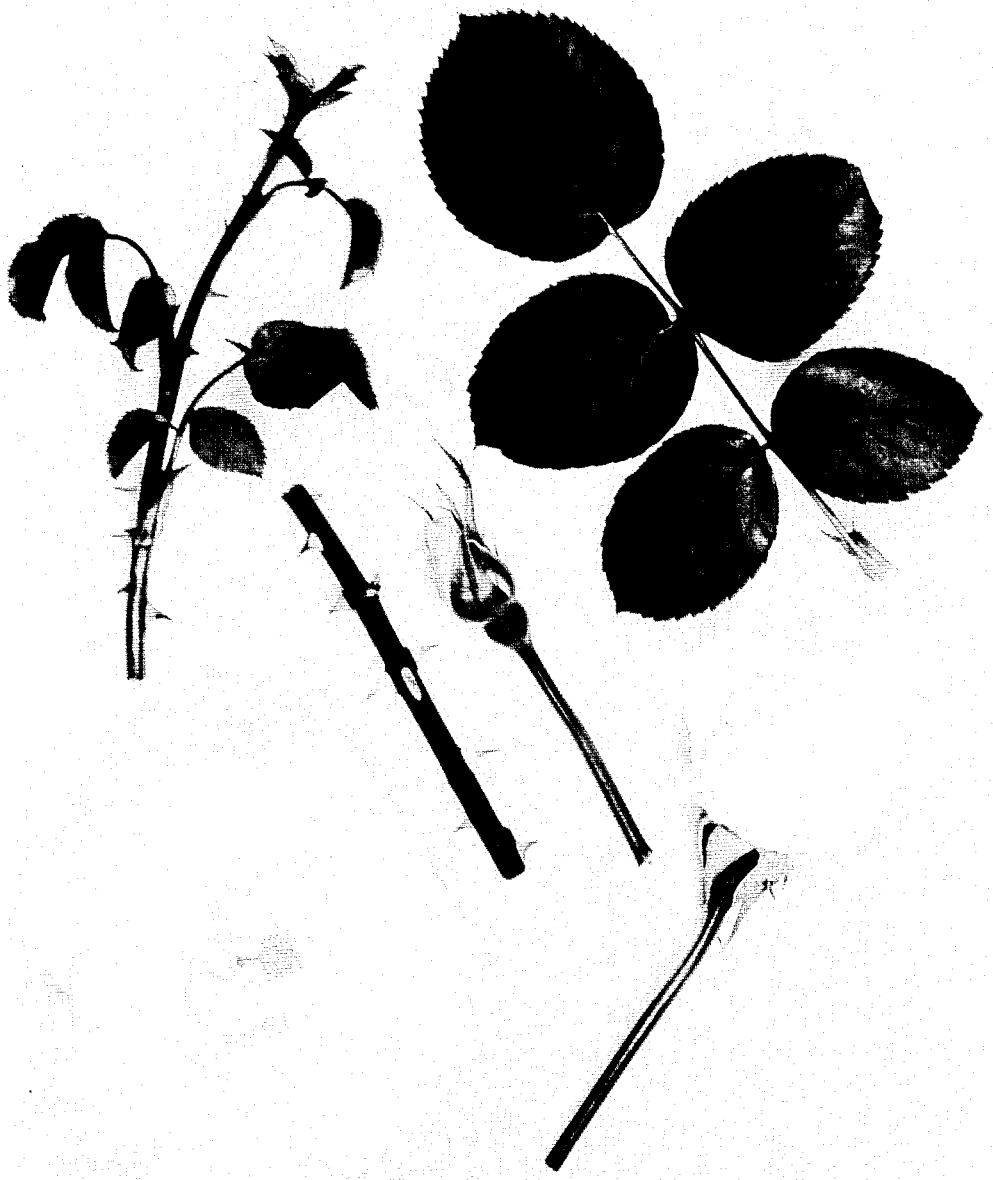
Inventor.
E. S. Boerner, Deceased
By: Lincoln Rochester Trust Company
By: Edward L. Jenner, Trust Officer
and Roger L. Boerner
Executors
By: Robb & Robb, Attorneys.

United States Patent Office

Plant Pat. 2,979
Patented July 7, 1970

2,979
ROSE PLANT

Eugene S. Boerner, deceased, late of Benton, N.Y., by Lincoln Rochester Trust Co., New York, N.Y., and Roger L. Boerner, Milwaukee, Wis., executors, assignors to Jackson & Perkins Company, Newark, N.Y., a corporation of New York

Filed Sept. 6, 1968, Ser. No. 759,808
Int. Cl. A01h *5/00*
U.S. Cl. Plt.—15 1 Claim

The present invention relates to a new and distinct variety of rose plant of the hybrid tea class, which was originated by the late Eugene S. Boerner, deceased, by crossing the rose variety known as "Golden Chalice" (Plant Pat. No. 1,958) with an unnamed and unpatented seedling of the rose variety known as "Golden Garnette" (Plant Pat. No. 1,898) × an unnamed and unpatented seedling of unidentified parentage.

The primary objective of this breeding was to produce a new and improved yellow-flowered hybrid tea rose variety suitable for use as a greenhouse cut flower variety. This objective was fully achieved, along with other desirable features, as evidenced by the following unique combination of characteristics which distinguish the new variety from its parents, as well as from all other varieties:

(1) Continuous growth throughout the year, but somewhat slower growth during the winter months;
(2) Relatively long flower stems;
(3) Broadly elliptical, nearly round leaflets;
(4) Distinctive and attractive yellow flowers;
(5) Excellent suitability for greenhouse cut flower production; and
(6) Relatively high resistance to mildew.

Asexual reproduction of the new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature except where general color terms of ordinary dictionary significance are obvious:

Parentage: Seedling.
*Seed parent.*—"Golden Chalice."
*Pollen parent.*—An unnamed seedling of "Golden Garnette" × an unnamed seedling of unidentified parentage.

Classification:
*Botanic.*—Hybrid tea.
*Commercial.*—Hybrid tea.

FLOWER (Observations made from specimens grown in a greenhouse at Newark, N.Y. in the early afternoon during the month of July.)

Blooming habit: Continuity—continuous through winter in greenhouse.

Bud:
*Peduncle.*—Slender. Size—about 4 inches long. Color—Light Bice Green, Plate 17. Strength—semi-rigid.
*Before calyx breaks.*—Size—from 1 inch to 1¼ inch. Shape—pointed. Color—Light Bice Green, Plate 17.

*Sepals.*—Color: outer surface—Light Bice Green, Plate 17; inner surface—Light Bice Green, Plate 17, with whitish tomentum. Length—from 1 inch to 1½ inches. Surface: outer—smooth; inner—tomentose. Edge—2 smooth; 2 with foliaceous appendages on both sides; 1 with folicaeous appendage on one side.
*Color (as sepals separate).*—From Mustard Yellow, Plate 16 to Primuline Yellow, Plate 16.

Bloom:
*Opening flower.*—Shape—long bud, slightly urn-shaped. Size—from 1½ inches to 1¾ inches long.
*Open flower.*—Overall shape—round; open-centered. Size—from 3¼ inches to 4½ inches in diameter.
*Petals.*—Shape—nearly round. Quantity—from 25 to 35 petals. Substance—thick; strong. Color: Newly open—from Lemon Chrome, Plate 4 to Pinard Yellow, Plate 4; three-days open—from Barium Yellow, Plate 16 to Primrose Yellow, Plate 30.
*Petaloids.*—From 3 to 10 in number. Color—Lemon Chrome, Plate 4.
*Persistance.*—Drop off cleanly; petals hang on after cutting flowers for 4 to 6 days.

REPRODUCTIVE ORGANS

Stamens: Numerous; arranged orderly around receptacle.
Filaments: Color—Light Cadmium, Plate 4.
Anthers: Color—Light Cadmium, Plate 4.
Styles:
*Color.*—Shading from cream at base to pink near stigmas.
*Arrangement.*—Uneven length; irregular shape.
Stigmas: Color—Martius Yellow, Plate 4.
Pollen: Sparse. Color—Martius Yellow, Plate 4.
Hips: Seeds borne internally.
Ovaries: Enclosed in receptacle.
Seeds: Partially exposed.

PLANT

Habit: Upright; from medium to above average size when grown in greenhouse, but small size when grown outdoors.
Disease resistance: Very good resistance to the usual rose diseases, particularly mildew, as determined from comparison with other varieties grown under the same conditions at Newark, N.Y.

Foliage:
*Leaves.*—Compound of 3 and 5 leaflets.
*Leaflets.*—Shape—nearly elliptical. Edge—irregularly serrated, with pointed apex. Color: upper side—Forest Green, Plate 17; lower side—Light Hellebore Green, Plate 17. Texture—medium thickness. Appearance—semi-glossy surface.
*Rachis.*—Color—Forest Green, Plate 17. Thorns—very few.
*Stipules.*—Color—Bice Green, Plate 17. Shape—average size, with points of medium width angled from rachis about 45°.

Stems:
*Color (with flowers developed).*—Forest Green, Plate 17.
*Old stems.*—Color—Yew Green, Plate 31.
*Texture.*—Smooth.

New Growth: Color—Claret Brown, Plate 1.

Thorns:
*Quantity.*—Few.
*Shape.*—Long base, with long point angled downward approximately 25°.
*Color.*—Young—Light Cress Green, Plate 31. Old—Russet, Plate 15.

What is claimed is:

1. A new and distinct variety of rose plant of the hybrid tea class, substanctially as herein shown and described, characterized particularly as to novelty by the unique combination of continuous growth throughout the year, but somewhat slower growth during the winter months, relatively long flower stems, broadly elliptical, nearly round leaflets, distinctive and attractive yellow flowers, excellent suitability for greenhouse cut flower production, and relatively high resistance to mildew.

No references cited.

ROBERT E. BAGWILL, Primary Examiner